United States Patent [19]

De Simone

[11] Patent Number: 4,665,254

[45] Date of Patent: May 12, 1987

[54] AMS-1B CRYSTALLINE BOROSILICATE MOLECULAR SIEVE-BASED CATALYST COMPOSITIONS AND PROCESS FOR XYLENE METHYLATION

[75] Inventor: Richard E. De Simone, Lisle, Ill.

[73] Assignee: Amoco Corporation, Chicago, Ill.

[21] Appl. No.: 801,603

[22] Filed: Nov. 25, 1985

[51] Int. Cl.$^4$ .............................................. C07C 2/68
[52] U.S. Cl. .................................................. 585/467
[58] Field of Search ........................................ 585/467

[56] References Cited

U.S. PATENT DOCUMENTS 4,491,678  1/1985  Oda et al. ............................ 585/467
4,520,219  5/1985  Sato .................................... 585/462

Primary Examiner—Curtis R. Davis
Attorney, Agent, or Firm—Reed F. Riley; William H. Magidson; R. C. Medhurst

[57] ABSTRACT

Disclosed are improved HAMS-1B crystalline molecular sieve-based catalyst compositions made by impregnating such a sieve, which has been incorporated in an inorganic matrix, with a small amount of a magnesium compound, and a process for employing such catalyst compositions for the methylation of a xylene in which the amount of pseudocumene in the product is substantially enhanced compared to that produced by the unimpregnated catalyst composition.

7 Claims, No Drawings

AMS-1B CRYSTALLINE BOROSILICATE MOLECULAR SIEVE-BASED CATALYST COMPOSITIONS AND PROCESS FOR XYLENE METHYLATION

BACKGROUND OF THE INVENTION

This invention relates to improved AMS-1B crystalline molecular sieve-based catalyst compositions, and particularly, to the use of such compositions having improved ability to form pseudocumene by the methylation of xylenes.

In U.S. Pat. Nos. 4,504,690, 4,128,592 and 4,086,287 is taught modifying a ZSM-5 aluminosilicate zeolite catalyst with P, Mg or P/Mg oxides to obtain high proportions of the 1,4-dialkyl isomer. Phosphorus or Mg modified ZSM-5 zeolite catalysts for the disproportionation of toluene are shown in J. Appl. Polym. Sci. 36, 209 (1981). Disproportionation of toluene to produce benzene over a P, Mg modified crystalline aluminosilicate zeolite catalyst is described in U.S. Pat. No. 4,137,195. Alkylation or disproportionation of certain monosubstituted benzene compounds to achieve nearly 100% selectivity to para-disubstituted derivatives over magnesium compound-modified ZSM-5 aluminosilicate zeolite catalysts is reported in J. Am. Chem. Sec. 101, 6783 (1979).

Use of Mg alone or in combination with P to modify a ZSM-5 aluminosilicate of zeolite catalyst is described in U.S. Pat. No. 4,049,573 and the modified catalyst used for converting alcohols and ethers to hydrocarbons. Again, Mg is used to modify ZSM-5 zeolite catalysts in U.S. Pat. No. 4,002,698 which can be used for selective production of p-xylene from charge stocks of toluene and a $C_3$–$C_{10}$ olefin.

Catalyst compositions, generally useful for hydrocarbon conversion, based upon AMS-1B crystalline borosilicate molecular sieve have been described in U.S. Pat. Nos. 4,268,420, 4,269,813, 4,285,919 and Published European Application No. 68,796.

As described in the references in the paragraph above, catalyst compositions typically are formed by incorporating an AMS-1B crystalline borosilicate molecular sieve material into a matrix such as alumina, silica or silica-alumina to produce a catalyst formulation. In one method of making AMS-1B crystalline borosilicate, sieve is formed by crystallizing sources for silicon oxide and boron oxide with sodium hydroxide and an organic compound. After crystallization, the resulting sodium form is ion exchanged with an ammonium compound and calcined to yield the hydrogen form of AMS-1B. In another more preferred method, AMS-1B crystalline borosilicate is crystallized in the hydrogen form from a mixture containing a diamine in place of a metal hydroxide. AMS-1B borosilicates in hydrogen form are designated HAMS-1B. Typically, the hydrogen form sieve is gelled with an alumina sol, dried and calcined to yield a catalyst composition.

SUMMARY OF THE INVENTION

Described herein are improved AMS-1B crystalline borosilicate molecular sieve-based catalyst compositions made by impregnating such a sieve, which has been incorporated in a matrix, with a small amount of a suitable magnesium compound, and processes for employing such catalyst compositions for the methylation of a xylene in which the amount of pseudocumene in the product is substantially enhanced compared to that produced by the unimpregnated composition.

DETAILED DESCRIPTION OF THE INVENTION

In the method of this invention a HAMS-1b crystalline molecular sieve incorporated into an inorganic matrix is impregnated with a small amount of magnesium oxide by treating with a solution of a magnesium compound, drying, and calcining the resulting impregnated catalyst composition at an elevated temperature. Impregnated compositions when contacted at elevated temperature with a mixture of a xylene and a methylating agent such as methanol or dimethylether can form enhanced amounts of pseudocumene compared to unimpregnated catalyst compositions.

To make an impregnated catalyst composition of this invention, a composition comprising the acid form of the crystalline borosilicate, HAMS-1B, molecular sieve in an inorganic matrix is contacted with a magnesium compound-containing solution. The resulting mass is dried at temperatures up to about 150° C. driving off in this step essentially all of the impregnation solvent. The resulting composition is then activated by calcination for about 1 hour to about 24 hours at temperatures between about 300° C. and about 800° C., more preferably, about 4 hours to about 24 hours at a temperature between about 400° C. to about 600° C.

The amount of magnesium incorporated with the catalyst composition should be from about 4% to 25% by weight, more preferably, from about 8% to about 15% by weight, percents calculated as percent magnesium. The incorporated magnesium is believed to be present substantially in the oxide form.

Preferred magnesium compounds include most soluble magnesium salts, more preferably, magnesium nitrate or acetate is used.

The solutions of magnesium compounds used in impregnation may be made from polar or nonpolar solvents, including water and organic solvents generally. Solvents that are destructive of either the zeolite or matrix should be avoided. Water and alcohol are preferred solvents.

The catalyst compositions used in this invention are based on AMS-1B crystalline borosilicate molecular sieve, which is described in U.S. Pat. Nos. 4,268,420, 4,269,813, and 4,285,919 and Published European Patent Application No. 68,796, all incorporated herein by reference. AMS-1B crystalline borosilicate generally can be characterized by the X-ray pattern listed in Table A and by the composition formula:

$$0.9 \pm 0.2 M_{2/n}O : B_2O_3 : ySiO_2 : zH_2O$$

wherein M is at least one cation, n is the oxidation state of the cation, y is between 4 and about 600 and z is between 0 and about 160.

TABLE A

| d-Spacing Å (1) | Assigned Strength (2) |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |

TABLE A-continued

| d-Spacing Å (1) | Assigned Strength (2) |
|---|---|
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

| | Broad | Preferred | Most Preferred |
|---|---|---|---|
| $SiO_2/B_2O_3$ | 5-400 | 10-150 | 10-80 |
| $R_2O^+/[R_2O^+ + M_{2/n}O]$ | 0.1-1.0 | 0.2-0.97 | 0.3-0.97 |
| $OH^-/SiO_2$ | 0.01-11 | 0.1-2 | 0.1-1 |
| $H_2O/OH^-$ | 10-4000 | 10-500 | 10-500 | wherein R is an organic compound and M is at least one cation having the oxidation state n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not cirtical although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate molecular sieve can be prepared by crystallizing a mixture of sources for an oxide of silicon, an oxide of boron, an alky ammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.1 and most preferably about 0.2 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50°-225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is neccessary, if it is desired to remove this material from the final product. Typically, mildly dried product is calcined at temperatures ranging from about 260° C. to about 850° C. and preferably about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form. If the sieve was prepared using a metal hydroxide, such as sodium hydroxide, the hydrogen form typically, is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Examples of catalytically active elements include ruthenium, rhodium, iron, cobalt, and nickel. Mixtures of elements can be used. Other catalytic materials include ions and compounds of aluminum, lanthanum, molybdenum, tungsten, and noble metals such as ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, cobalt, iron, zinc and cadmium. Specific combinations of non-noble metals of Group VIII and other catalytic materials include ions or compounds of nickel and osmium, nickel and lanthanum, nickel and palladium, nickel and iridium, nickel and molybdenum, and nickel and tungsten.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide like alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. The optimum amount can be determined easily by routine experimentation.

The AMS-1B crystalline borosilicate useful in this invention is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt.% of the total composition. Catalytic compositions can contain about 0.1 wt.% to about 100 wt.% crystalline borosilicate material and preferably contain about 10 wt.% to about 95 wt.% of such material and most preferably contain about 20 wt.% to about 80 wt.% of such material.

Catalyst compositions treated with a magnesium compound according to this invention can be in powder form or already in extrudate form.

Methylation of xylene in the presence of the above described catalyst is effected by contact of a xylene with a methylating agent, preferably methanol or dimethylether, at a temperature between about 250° C. and about 750° C. and preferably between about 500° C. and about 700° C. The reaction generally takes place at atmospheric pressure, but the pressure range may be within the approximate range of about 1 atmosphere to about 2000 psig. The molar ratio of methylating agent to xylene is generally between about 0.5 and about 5. When methanol is employed as the methylating agent a suitable molar ratio of methanol to toluene has been found to be approximately about 0.1–1 mols of methanol per mol of toluene. With the use of other methylating agents, such as methylchloride, methylbromide, dimethylether, methylcarbonate, light olefins or dimethylsulfide, the molar ratio of methylating agent to toluene may vary within the aforenoted range.

Reaction is suitably accomplished utilizing a weight hourly space velocity of between about 1 and about 1000 and preferably between about 5 and about 500. The reaction product consisting predominantly of xylene and tri and tetramethyl benzenes may be separated by any suitable means, such as by passing the same through a distillation column.

The following Examples will serve to illustrate certain specific embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

All methylation reactions in Examples 3 and 4 below were carried out in a stainless steel reactor of plug flow design. A mixture of the appropriate xylene and methanol (4:1 mol ratio) was introduced at atmospheric pressure into a preheater packed with inert Denstone packing. Reactants were then passed into a ½" O.D.×5" reactor tube filled with approximately 5 g of catalyst. The entire reactor and preheater assembly was supported in a fluidized-bed sand bath maintained at reaction temperature. Product was collected in a cooled vessel as it dripped from the reactor and was analyzed by gas chromatography on a 60-meter fused silica capillary column. Magnesium contents are given in weight percent of the element.

COMPARATIVE EXAMPLE 1

The catalyst composition of this Example was made from 40% HAMS-1B crystalline borosilicate and 60% alumina. A 118 g portion of HAMS-1B was gelled with a 1810 g portion of American Cyanamide PHF alumina sol that has a 9.47% by weight content of alumina, using 171 ml of concentrated ammonium hydroxide (29% $NH_3$) and 236 g of water. The gel was dried at 165° C. for 18 hours. The dried sample was ground to 18–40 mesh then calcined at 538° C. for 12 hours.

EXAMPLE 2

A 6.0 g portion of the catalyst composition of Example 1 in the form of 1/16" extrudates was placed in a solution of 8.27 g $Mg(NO_3)_2 \cdot 6H_2O$ dissolved in 15 ml of water. The mixture was heated in a water bath at 92° C. for one hour, cooled and stirred for an additional two hours, and then left undisturbed overnight. After 1½ hours in a drying oven at 110° C. to remove bulk water, the catalyst was placed in a calcining oven. The temperature of the oven was slowly increased at ½ hour intervals until 500° C. was reached, and held at this temperature overnight. Upon cooling the catalyst composition was ready for use and contained about 10% by weight magnesium.

COMPARATIVE EXAMPLE 3

A catalyst composition charge of 4 g of the catalyst composition of Example 1 was placed in the reactor and heated to 400° C. under a stream of argon. The appropriate xylene/methanol mixture was fed at a rate of 0.21 ml/min. for a period of 90 minutes whereupon the sampling was completed. The temperature was raised to 500° C. and sampling continued for a further 90 minutes. In the Table below are recorded selectivity data and other conditions for runs 1–8 carried out as in this Example.

EXAMPLE 4

All the reactions in this Example were carried out as in Example 3 except that the impregnated catalyst composition of Example 2 was used. The selectivity data and other conditions are presented in the Table below for runs 9–14 carried as in this Example.

TABLE

| Run No. | Catalyst Example No. | Reactor T (°C.) | Feed | % Pseudocumene In Trimethylbenzene Fraction | Ratio Trimethyl/ Tetramethylbenzene |
|---|---|---|---|---|---|
| Example 1* | 1 | 500 | p-xylene | 64 | 91/9 |
| 2* | 1 | 500 | o-xylene | 59 | 95/5 |
| 3* | 1 | 500 | m-xylene | 66 | 92/8 |
| 4* | 1 | 500 | mixed xylene | 67 | 90/10 |
| 5 | 1 | 400 | p-xylene | 67 | 91/9 |
| 6 | 1 | 500 | p-xylene | 66 | 94/6 |
| 7 | 1 | 400 | mixed xylenes | 66 | 91/9 |
| 8 | 1 | 500 | mixed xylenes | 64 | 93/7 |
| 9* | 2 | 400 | p-xylene | 98 | 91/9 |
| 10 | 2 | 400 | p-xylene | 97 | 92/8 |
| 11* | 2 | 500 | p-xylene | 90 | 94/6 |
| 12 | 2 | 500 | p-xylene | 91 | 95/5 |
| 13 | 2 | 400 | mixed xylenes | 82 | 91/9 |
| 14 | 2 | 500 | mixed xylenes | 75 | 93/7 |

*Catalyst composition was calcined during methylation reaction.

What is claimed is:

1. A process for making pseudocumene comprising methylating a xylene in the presence of a catalyst composition comprising a HAMS-1B crystalline borosilicate molecular sieve incorporated into an inorganic matrix, said composition impregnated by a magnesium compound and subsequently heated to substantially convert said compound to the oxide form.

2. A process for making pseudocumene comprising methylating a xylene in the presence of the catalyst composition of claim 1 containing between about 0.5 and about 25 weight percent magnesium.

3. A process for making pseudocumene comprising methylating a xylene in the presence of the catalyst composition of claim 1 containing between about 8 and about 15 weight percent magnesium.

4. A process for making pseudocumene comprising methylating a xylene in the presence of the catalyst composition of claim 2 wherein said HAMS-1B moleuclar sieve comprises from about 20 to about 80 wt.% incorporated into an alumina, silica or silica-alumina matrix.

5. A process for making pseudocumene comprising methylating a xylene in the presence of the catalyst composition of claim 3 wherein said HAMS-1B molecular sieve comprises from about 20 to about 80 wt.% incorporated into an alumina, silica or silica-alumina matrix.

6. A process for making pseudocumene comprising reacting methanol or dimethylether with a xylene in the presence of the catalyst composition of claim 4.

7. A process for making pseudocumene comprising reacting methanol or dimethylether with a xylene in the presence of the catalyst composition of claim 5.

* * * * *